US008819862B2

(12) United States Patent
Shaw

(10) Patent No.: US 8,819,862 B2
(45) Date of Patent: Sep. 2, 2014

(54) SUNGLASSES WITH FLIP-UP VISOR

(76) Inventor: Andrew Robert Shaw, Dickson, TN (US)

( * ) Notice: Subject to any disclaimer, the term of this patent is extended or adjusted under 35 U.S.C. 154(b) by 420 days.

(21) Appl. No.: 13/136,910

(22) Filed: Aug. 15, 2011

(65) Prior Publication Data

US 2011/0296575 A1    Dec. 8, 2011

Related U.S. Application Data

(63) Continuation-in-part of application No. 12/229,441, filed on Aug. 22, 2008, now abandoned.

(51) Int. Cl.
*A61F 9/00* (2006.01)
*G02C 9/02* (2006.01)
*A61F 9/02* (2006.01)

(52) U.S. Cl.
CPC .. *A61F 9/025* (2013.01); *G02C 9/02* (2013.01)
USPC ................................................. 2/12; 351/155

(58) Field of Classification Search
USPC .................... 2/10, 12, 13; 351/51, 59, 155
See application file for complete search history.

(56) References Cited

U.S. PATENT DOCUMENTS

| 2,481,960 | A | * | 9/1949 | Wall et al. | 2/10 |
| 2,691,165 | A | * | 10/1954 | Kane | 2/13 |
| 5,258,786 | A | * | 11/1993 | Penrod | 351/47 |
| 5,347,655 | A | * | 9/1994 | Garrett | 2/10 |
| 5,438,378 | A | * | 8/1995 | Blatter | 351/47 |

* cited by examiner

*Primary Examiner* — Katherine Moran
(74) *Attorney, Agent, or Firm* — Harry I. Eon; Vivian L. Steadman

(57) ABSTRACT

A flip-up visor attachment having two separable sets of hinge elements for rotatably connecting the visor to a sunglasses' frame. These sets include a hinge body and a pair of hook-like structures which are, respectively, affixed to the frame's bridge portion and to the visor's underside. Like the frame, both sets exhibit bilateral symmetry. Once they are joined together, the visor can be pivoted outwardly from the frame's front. A flange, affixed to the visor's mid-section and extending over its back edge, stops the visor from being overrotated. With the visor in its raised position, one can then brace it there by pressing a locking arm rotatably connected to its underside against the hinge body. By rotating the locking arm in reverse, one can disengage it from the hinge body and thus free the visor so that it can be folded against the sunglasses or removed therefrom.

7 Claims, 4 Drawing Sheets

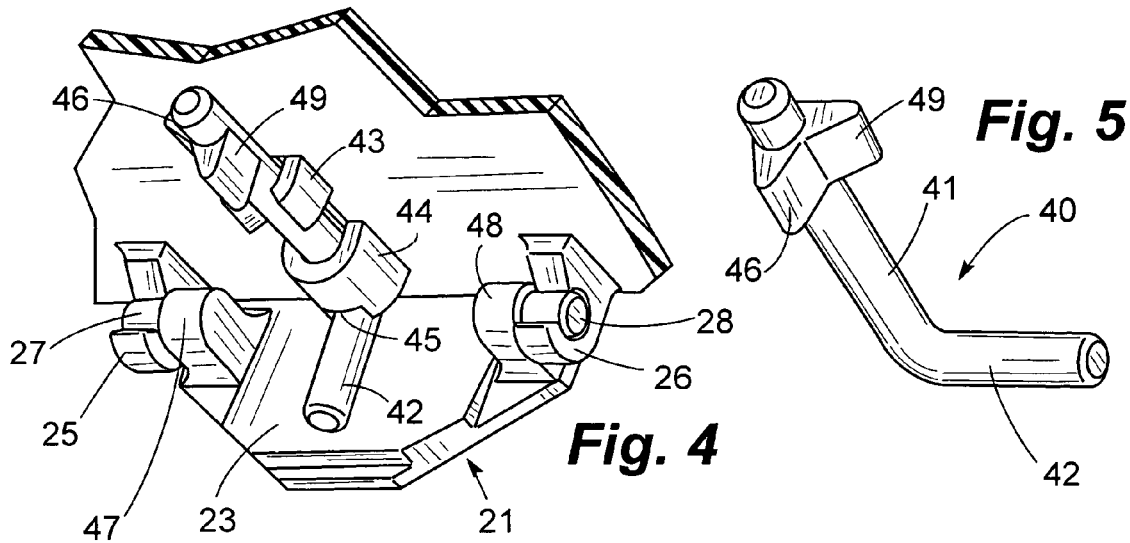
Fig. 4
Fig. 5
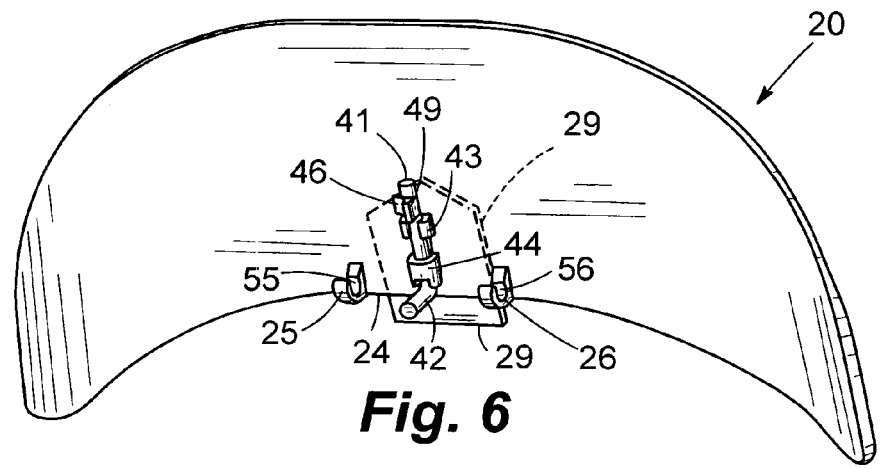
Fig. 6
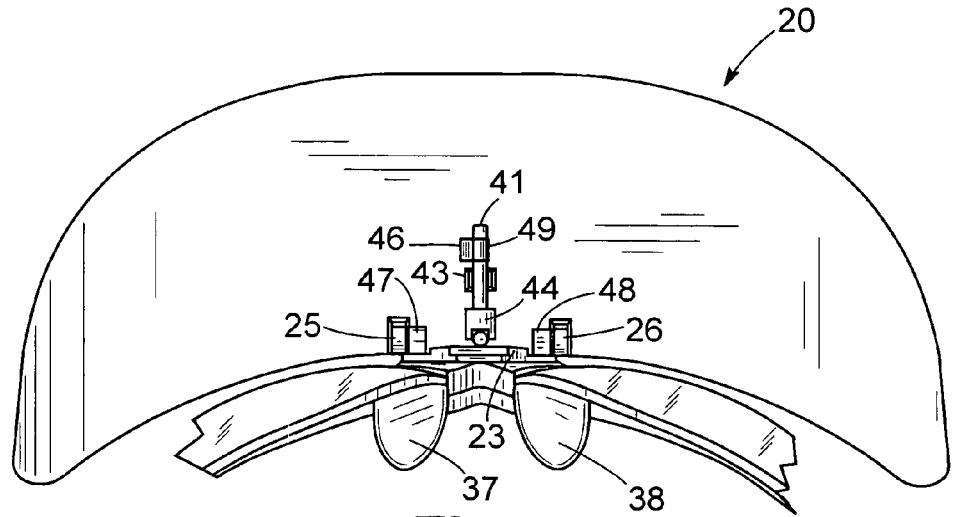
Fig. 7

SUNGLASSES WITH FLIP-UP VISOR

CROSS-REFERENCE TO RELATED APPLICATION

This is a continuation-in-part application of my U.S. patent application having Ser. No. 12/229,441, filed on Aug. 22, 2008 now abandoned.

FIELD OF THE INVENTION

The present invention relates generally to eye protection and more specifically to attachments for eyeglasses.

BACKGROUND OF THE INVENTION

Combinations of visors with eyeglasses, such as that taught by Wall (U.S. Pat. No. 2,481,960) in which the visor, when fixedly attached to the bridge portion of a pair of eyeglasses, occupies a position extending from above the bridge portion, are well known in the prior art.

The previous art, however, fails to teach a visor and eyeglasses combination wherein not only is the visor removably attached to the eyeglasses in such a way that the eyeglasses can be worn separately without compromising their aesthetic appeal, but also the visor, while still attached to the eyeglasses, can be rotated into a position in which it is substantially folded against the lenses of the eyeglasses, thereby facilitating storage of the visor and eyeglasses combination.

SUMMARY OF THE INVENTION

The primary object of this invention is to provide a visor and eyeglasses combination in which the visor is alternately rotatably connected to the frame of the eyeglasses and fixedly attached thereto, and wherein structures for rotatably connecting the visor and frame together in assembled relation are so configured that the visor can be rotated into a position in which a person, without the use of tools, can readily disengage the visor from the frame.

A further object of the invention is to provide such a visor and eyeglasses combination which can be folded into minimum volume for easy storage.

A still further object of the invention is to provide such a visor and eyeglasses combination in which the eyeglasses can be used independently of the visor.

Yet a further object of the invention is to provide such a visor and eyeglasses combination having interchangeable visors and/or interchangeable eyeglasses.

In accordance with the present invention, there is provided a visor and eyeglasses combination which comprises means, including a hinge, for rotatably connecting the visor to the frame of the eyeglasses, a stop for limiting the visor's upward rotation, and a locking arm.

Joined together in assembled relation to form the hinge are two separable sets of hinge elements. In the preferred embodiment, the first of these sets is affixed to the underside of the visor's mid-section proximate with the visor's back edge; and the second of these sets is defined by a bridge piece permanently anchored to the bridge portion of the eyeglasses. Preferably, the hinge elements in the first set, when so affixed, exhibit bilateral symmetry as do the hinge elements of the second set and the bridge piece itself.

In addition, the bridge piece preferably defines both a riser and a wedge, the latter having a taper of increasing thickness in a direction away from the riser and its juncture with the wedge. This juncture, when the visor is fixedly attached to the frame of the eyeglasses, is disposed generally parallel to the back edge of the visor's mid-section and contiguous therewith.

The stop for limiting the visor's upward rotation comprises a flange which is preferably affixed to the upper side of the visor's mid-section and cantilevered over the visor's back edge. The flange abuts the bridge portion of the eyeglasses' top edge once the visor, as it is being rotated upwardly about the hinge, reaches the upper limit of its travel.

The locking arm, which includes a shaft with a short arm disposed perpendicularly thereto, is rotatably connected to the visor's underside by bearings mounted thereon. One of these bearings terminates in an open-ended, shallow notch. Disposed proximate with the visor's back edge and away from the interface between the visor and the bearing which defines the notch, the latter is sized for receiving a portion of the short arm, so that once the arm has been rotated downwardly across the bridge piece, said portion of the arm can be held generally perpendicularly to the visor whenever the visor, whether in service or just readied for use, extends outwardly from the frame of the eyeglasses. Because of the bridge piece's wedge with its downwardly-directed increase in thickness, said portion of the short arm, upon its being received within the shallow notch, effectively springs into place there and locks itself within the notch, thereby forming a stable brace between the visor and the bridge piece.

BRIEF DESCRIPTION OF THE DRAWINGS

FIG. 4 is a perspective view, on a further enlarged scale, of a fragmentary portion of the visor's mid-section, as well as of the visor's locking arm and of a bridge piece which, in assembled relation, is affixed to the sunglasses, the locking arm being shown in position for bracing the raised visor;

FIG. 5 is a perspective view, on a still further enlarged scale, of the locking arm according to FIG. 4;

FIG. 6 is a perspective bottom view, on an enlarged scale, of the flip-up visor in the combination according to FIG. 1, the visor being shown by itself, detached from the sunglasses, but with the locking arm in its locked position; a portion of the flange disposed contiguous with the visor's upper surface being shown in broken lines;

FIG. 7 is a bottom plan view, on an enlarged scale, of the flip-up visor and a fragmentary portion of the sunglasses in the combination according to FIG. 1, with the visor being shown in its raised position;

DETAILED DESCRIPTION OF THE PREFERRED EMBODIMENT

Figure 3:
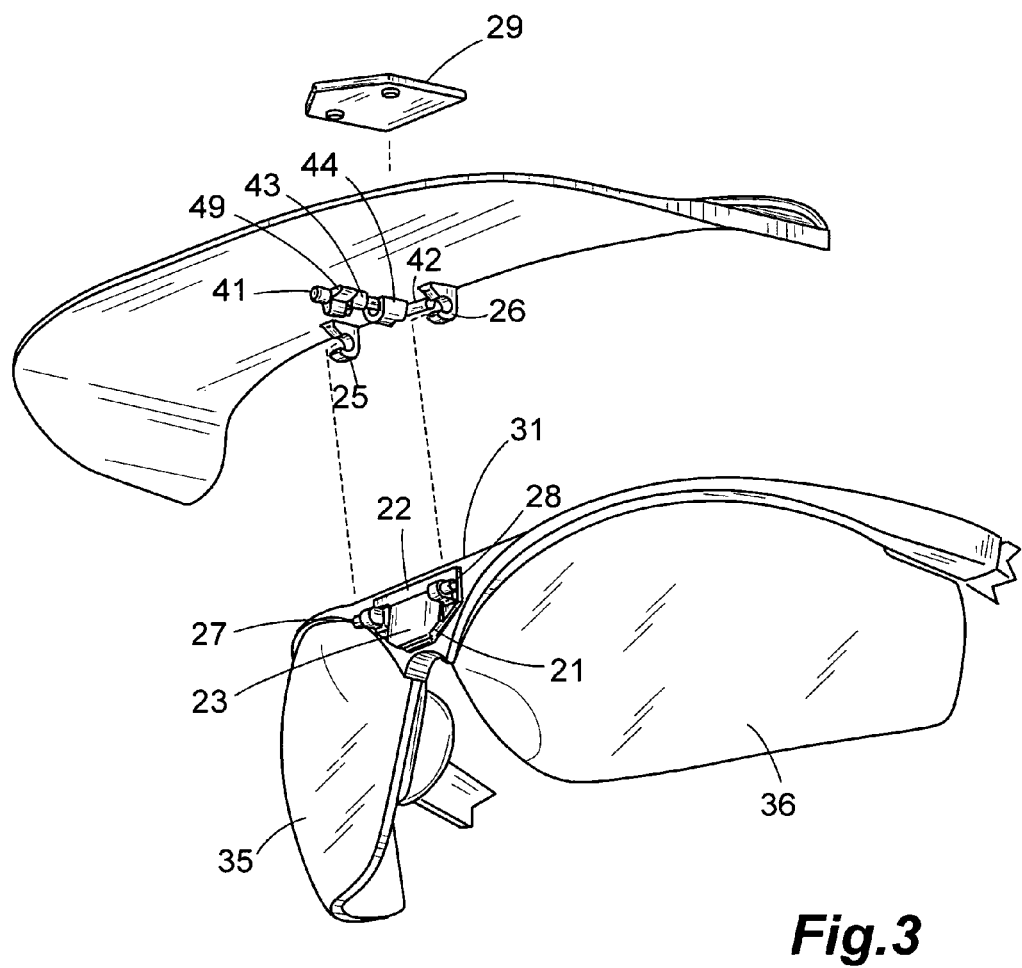
FIG. 3 is a partially exploded view, on an enlarged scale, of the flip-up visor and sunglasses combination according to FIG. 1, with the visor's locking arm being shown in its release position.
Figure 8:
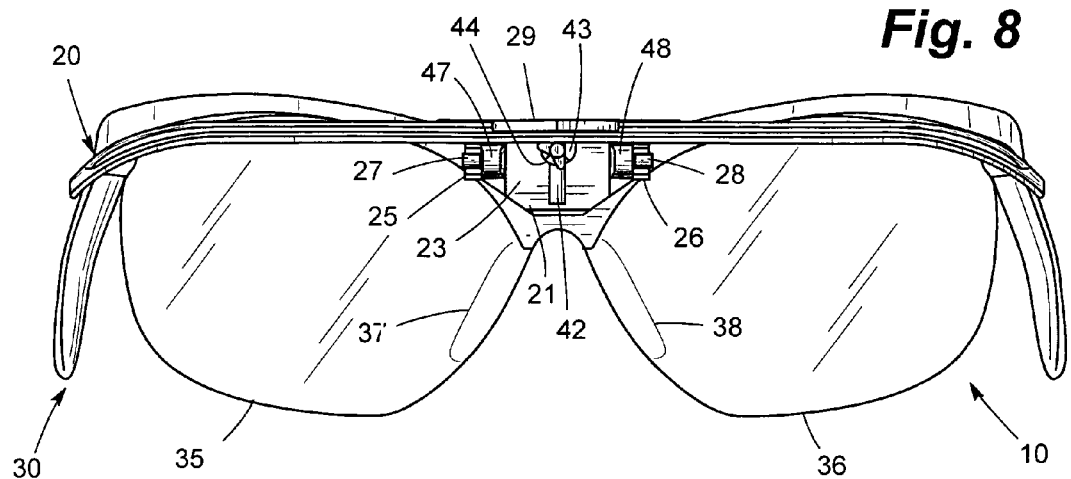
FIG. 8 is a frontal perspective view of the flip-up visor and sunglasses combination according to FIG. 1, with the visor being shown in its raised position.
Figure 10:
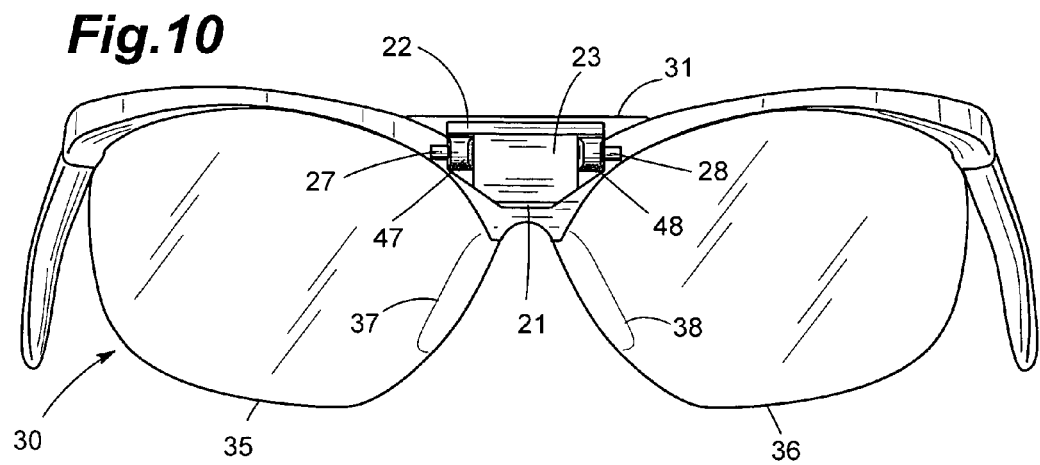
FIG. 10 is a frontal perspective view of the sunglasses in the combination according to FIG. 1, with the visor having been removed and with only the bridge piece still attached to the sunglasses.

In the drawings, a sunglasses with flip-up visor according to the present invention is indicated generally by the reference numeral 10. The assembly 10 is an exemplary embodiment of the invention, which may be embodied in various forms, including a wide variety of sunglasses 30 which have an ample bridge portion 31 (FIGS. 3, 8 and 10). Such a bridge portion 31 serves as a base onto which is affixed, with the use of either a mechanical fastener (not shown) or an adhesive, a bridge piece 21.

The bridge piece 21 is part of a hinge having two separable sets of hinge elements (FIGS. 3 and 4). Preferably, the first of these sets includes a pair of spaced apart, hook-like structures 25, 26 which are affixed to the underside of the visor's mid-section proximate with the visor's back edge 24; and the second of these sets is a pair of spaced apart pins 27, 28, which extend coaxially and in opposite directions from their respective mounts 47, 48 on the bridge piece 21 (FIGS. 3, 4, 6-8 and 10). Moreover, the hook-like structures 25, 26 define gaps 55, 56 for receiving the pins 27, 28, respectively, and are configured in such a way that, in assembled relation, the pins, once they have been slip-fitted into the gaps, continue to be rotatably held there, even as the visor is pivoted upwardly about an axis which extends along the pins' longitudinal centerlines (FIG. 4).

Figure 9:
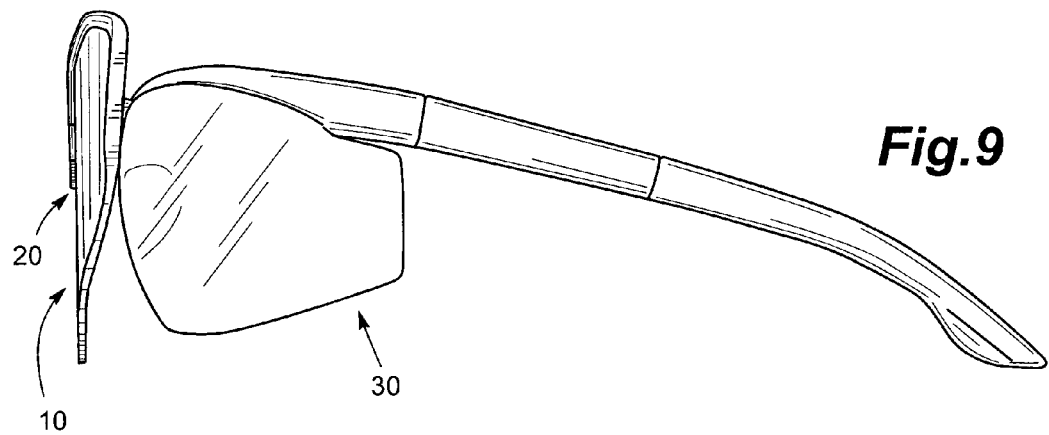
FIG. 9 is a side elevation view of the flip-up visor and sunglasses combination according to FIG. 1, with the visor in the folded position.

Assembly of the combination 10 entails holding the visor 20 and the sunglasses 30 together in a configuration consistent with that into which they are folded whenever the visor, rotatably connected to the sunglasses frame, reaches the limit of its downward travel about said pivot axis (FIG. 9). With the visor 20 and the sunglasses 30 thus held, both of the pins 27, 28 can then be aligned with the gaps 55, 56 and slip-fitted into them. Alternately, the pins 27, 28 can be removed from the gaps 55, 56 when the visor 20 and the sunglasses 30 are arrayed in this same folded configuration, thereby allowing the user to wear the sunglasses independently of the visor, even though the bridge piece 21 is still affixed to the bridge portion 31 (FIG. 10).

In the preferred embodiment, the pins 27, 28 and their respective mounts 47, 48 are integral parts of the bridge piece 21 and form a single, unitary body with it (FIG. 4). Moreover, in the combination 10, the pair of hook-like structures 25, 26 and the bridge piece 21, when affixed to the visor's underside and to the sunglasses' bridge portion 31, respectively, exhibit bilateral symmetry consistent with that of the sunglasses' frame, nosepiece support elements 37, 38, and lenses 35, 36 (FIG. 8).

Also defined by the bridge piece 21 is a wedge 23. The latter has a taper of increasing thickness in a direction away from the pins 27, 28 and their mounts 47, 48 (FIG. 4). Moreover, atop the bridge piece 21 in the preferred embodiment is a riser 22. Joined to the wedge 23, the riser 22, like the wedge, is preferably an integral part of the bridge piece 21. When the visor 20 is fixedly attached to the frame of the sunglasses 30, the riser/wedge juncture is disposed generally parallel to the back edge 24 of the visor's mid-section and contiguous therewith, so that the mid-section's back edge can be pressed against the riser and held firmly in place there (FIGS. 4, 6 and 7).

Figure 1:
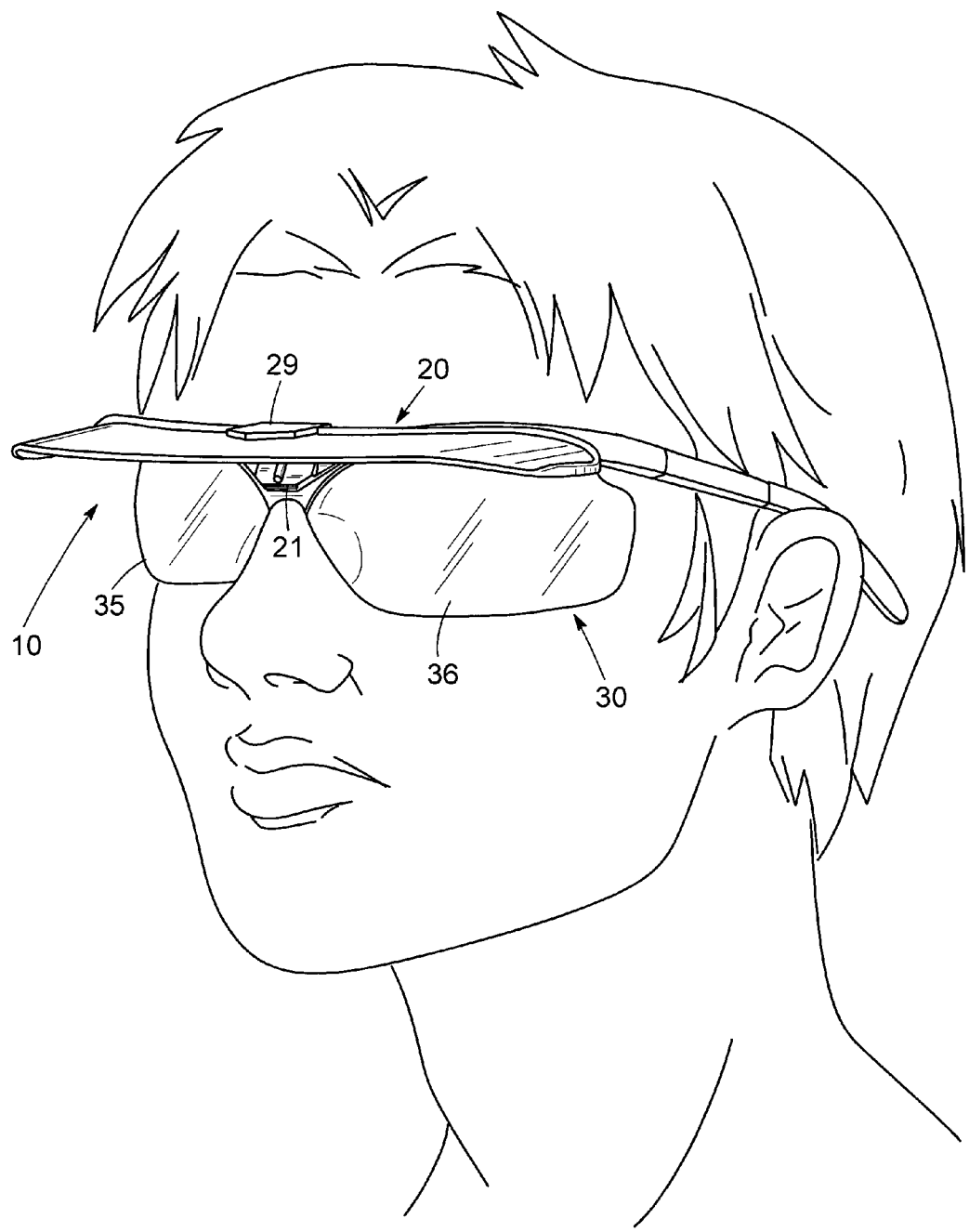
FIG. 1 is a frontal perspective view of a flip-up visor and sunglasses combination, according to the present invention, in use.
Figure 2:
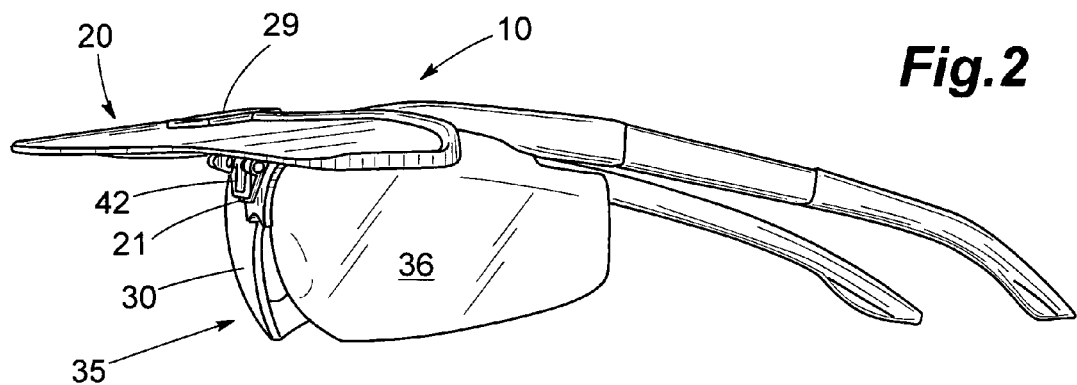
FIG. 2 is a side perspective view of the flip-up visor and sunglasses combination according to FIG. 1.

Upward rotation of the visor 20 about the hinge connecting it to the sunglasses' frame is limited by a stop (FIGS. 1, 3, 6, and 8). Included in the stop is a flange 29 which is preferably affixed to the upper side of the visor's mid-section. For a combination 10 in which the visor 20 features a rib-like structure running along the visor's back edge 24 and protruding upwardly therefrom, a shallow cutout (not shown) is preferably made in the rib-like structure so that the flange 29 can be mounted flush with the visor's mid-section when the flange is so affixed (FIGS. 1 and 8).

Cantilevered over the visor's back edge 24, the flange 29 extends rearwardly a sufficient distance therefrom that the flange's distal end rests on the bridge portion 31, pressing against its top edge, once the visor 20, as it is being rotated upwardly about the hinge, reaches the upper limit of its travel. Alternately, the bridge piece 21 can be affixed to the sunglasses' frame in such a way that the riser 22 extends a short distance upwardly of the bridge portion's top edge; then, instead of the flange's distal end resting on the bridge portion 31, said end abuts the riser.

During use, the visor 20 extends outwardly from the sunglasses' frame and is disposed generally perpendicularly to the lenses 35, 36 (FIG. 1). Means for holding the visor in position once its upward travel about the hinge has been stopped comprises a locking arm 40. Rotatably connected to the underside of the visor's mid-section by bearings 43, 44 mounted thereon, the locking arm 40 includes a shaft 41 with a short arm 42 disposed perpendicularly thereto and with cam elements 46, 49 affixed to the shaft distal from the short arm (FIGS. 4 and 5).

In addition to the locking arm 40, the means for holding the visor 20 in position for use includes an open-ended, shallow notch 45 defined by the bearing 44 (FIG. 4). Disposed proximate with the back edge 24 and directed away from the visor's interface with the bearing 44, the notch 45 is sized for receiving a portion of the short arm 42. By pushing on the cam 46, one can manually rotate the shaft 41 within its bearings 43, 44, and, with the visor 20 extending outwardly from the sunglasses' frame, simultaneously rotate the short arm 42 across the bridge piece 21. In the process, the short arm 42 is pressed against the bridge piece's wedge 23. Because of the wedge's increase in thickness in a direction away from the hinge's pivot, said portion of the short arm 42, upon its being received within the notch 45, effectively springs into place there and locks itself within the notch, thereby forming a stable brace between the visor 20 and the bridge piece 21.

Alternately, by pushing on the cam 49, one can manually rotate the shaft 41 within its bearings 43, 44 so as to free the short arm 42 from the wedge 23 and bring the short arm into a position in which it is disposed flush with the underside of the visor's mid-section (FIGS. 3 and 5). With the short arm 42 thus freed, one can then rotate the visor 20, folding it and the sunglasses 30 together for either storage or disengagement of the visor from the bridge piece 21.

What is claimed is:

1. In combination with a visor and a pair of eyeglasses in which the eyeglasses frame a pair of spaced apart lenses, the eyeglasses having a bridge portion which forms a span between the lenses, the span generally increasing in length towards the bridge portion's upper edge, and wherein the visor, which is generally bilaterally symmetrical, defines a mid-section with a back edge, (a) a hinge with a pivot axis which is disposed proximate with the bridge portion's upper edge, the hinge rotatably connecting the visor to the eyeglasses frame and having separable first and second sets of hinge elements, the hinge elements of the first set being affixed to the visor's mid-section;
   (b) a bridge piece affixed to the eyeglasses bridge portion, the hinge elements of the second set being mounted on the bridge piece;
   (c) means, including a flange affixed to the visor's mid-section and cantilevered rearwardly therefrom, for limiting the visor's upward rotation about the pivot axis, the flange abutting the bridge portion once the visor reaches the upper limit of its travel; and (d) wherein the hinge elements of the first and second sets, in assembled relation, are interconnected in such a way that the visor can be rotated downwardly about the pivot axis.

2. In combination with the visor and the pair of eyeglasses according to claim 1, a locking arm which is rotatably connected to the visor's mid-section, the locking arm, when engaged, bracing the visor's mid-section against the bridge piece; and wherein the locking arm comprises both an elongated shaft and a short arm disposed perpendicularly thereto, the shaft, in assembled relation, extending perpendicularly to the mid-section's back edge; and wherein the bridge piece defines a wedge, the wedge having a taper which increases in thickness in a direction away from, and which is oriented perpendicularly to, the hinge's pivot axis, the short arm being pressed against the wedge whenever the locking arm is engaged so as to brace the visor's mid-section against the bridge piece and perpendicularly thereto.

3. In combination with the visor and the pair of eyeglasses according to claim 1, a locking arm which is rotatably connected to the visor's mid-section, the locking arm, when engaged, bracing the visor's mid-section against the bridge piece; and wherein the locking arm comprises both an elongated shaft and a short arm disposed perpendicularly thereto, and wherein at least one bearing for rotatably connecting the locking arm to the visor's mid-section is mounted on the underside thereof in such a way that the shaft, when rotatably connected to the bearing, extends perpendicularly to the mid-section's back edge, the bearing defining an open-ended notch for receiving a portion of the short arm, and wherein the bridge piece defines a wedge, the wedge having a taper which increases in thickness in a direction away from, and which is oriented perpendicularly to, the hinge's pivot axis, said portion of the short arm being locked within the notch whenever the locking arm is engaged so as to brace the visor's mid-section against the bridge piece.

4. In combination with a visor and a pair of eyeglasses in which the eyeglasses frame a pair of spaced apart lenses, the eyeglasses having a bridge portion which forms a span between the lenses, the span generally increasing in length towards the bridge portion's upper edge, and wherein the bilaterally mid-section with a back edge, (a) a hinge with a pivot axis which is disposed proximate with the bridge portion's upper edge, the hinge rotatably connecting the visor to the eyeglasses frame and having separable first and second sets of hinge elements, the hinge elements of the first set being affixed to the visor's mid-section;

(b) a bridge piece affixed to the eyeglasses bridge portion, the hinge elements of the second set being mounted on the bridge piece;

(c) wherein the first set of hinge elements includes a pair of spaced apart, hook-like structures which define coaxially aligned, cylindroid gaps, each of the hook-like structures also defining an outwardly expanding passageway which communicates with the hook-like structure's gap and which is oriented perpendicularly to the hinge's pivot axis; and wherein the second set of hinge elements includes a pair of spaced apart, coaxially aligned pins which protrude from the bridge piece; and wherein each pin is individually received within one of the cylindroid gaps and rotatably coupled to the hook-like structure which defines the gap within which the pin is so received, the pin, prior to its being so coupled, having been guided through the hook-like structure's outwardly expanding passageway and then slip-fitted into the cylindroid gap which communicates therewith; and (d) wherein the hinge elements of the first and second sets, in assembled relation, are interconnected in such a way that the visor can be rotated downwardly about the pivot axis.

5. In combination with the visor and the pair of eyeglasses according to claim 4, wherein each hook-like structure's outwardly expanding passageway is further characterized as opening in a direction which is generally parallel to the visor mid-section's underside; and wherein portions of each hook-like structure which are disposed distal from the back edge of the mid-section and which define the hook-like structure's outwardly expanding passageway are spaced apart from said back edge by a distance which is substantially greater than the span separating the pin, which is rotatably coupled to said hook-like structure, from the bridge portion of the frame, so that the pins can be removed from said gaps by slipping them out only when the visor and the eyeglasses have been substantially folded together by rotating the visor downwardly about the pivot axis.

6. An eyeglasses with flip-up visor, which comprises:

(a) eyeglasses having a bridge portion with an upper edge;

(b) the visor, which generally exhibits bilateral symmetry, defining a mid-section with a back edge;

(c) a riser and a bridge piece permanently attached to the bridge portion, the riser forming a juncture with the bridge piece in front of the bridge portion and having a vertical face which extends upwardly from the juncture;

(d) a hinge, with a pivot axis which is disposed proximate with the bridge portion's upper edge and generally parallel to said juncture, the hinge having separable first and second sets of hinge elements, the hinge elements of the first set being mounted on the underside of the visor's mid-section, and the hinge elements of the second set being mounted on the bridge piece; the hinge elements of the first and second sets rotatably interconnecting the eyeglasses' frame and the visor so that it can be rotated outwardly from the front of the frame;

(e) wherein the hinge elements of the first set are spaced apart from each other by a span of the visor's mid-section, the span being sufficiently long that the span's back edge can abut the riser's vertical face and be disposed contiguous therewith once the visor has been rotated upwardly about the pivot axis and reached the upper limit of its travel; and (f) a locking arm which is rotatably connected to the visor's mid-section, the locking arm having both an elongated shaft and a short arm disposed perpendicularly thereto, the shaft, in assembled relation, extending perpendicularly to the mid-section's back edge; and (g) wherein the bridge piece defines a wedge which extends downwardly from the riser's juncture with the bridge piece, the wedge having a taper which increases in thickness in a direction away from, and which is oriented perpendicularly to, the hinge's pivot axis, the span's back edge being pressed against the riser at the same time the short arm is pressed against the wedge whenever the locking arm is engaged so as to brace the visor's mid-section against the bridge piece and perpendicularly thereto.

7. The eyeglasses with flip-up visor according to claim 6, wherein the hinge elements of the first set are further characterized as defining at least two spaced apart gaps for receiving the hinge elements of the second set which are individually and rotatably coupled to the hinge elements of the first set.

* * * * *